(12) United States Patent
Jones

(10) Patent No.: US 6,485,691 B1
(45) Date of Patent: Nov. 26, 2002

(54) COMBINED SPECIMEN CUP, LID AND DETACHABLE HANDLE

(76) Inventor: Timothy B. Jones, 7408 NE. 97th Ter., Oklahoma City, OK (US) 73151

( * ) Notice: Subject to any disclaimer, the term of this patent is extended or adjusted under 35 U.S.C. 154(b) by 247 days.

(21) Appl. No.: 09/648,994

(22) Filed: Aug. 28, 2000

(51) Int. Cl.[7] ................................................. B02L 3/00
(52) U.S. Cl. ........................ 422/102; 422/99; 220/694; 220/735; 220/752; 220/756; 220/761
(58) Field of Search ............................. 422/58, 61, 99, 422/102; 220/696, 697, 699, 735, 752, 759, 756, 761, 770, 767–769

(56) References Cited

U.S. PATENT DOCUMENTS

| | | | | |
|---|---|---|---|---|
| 3,275,187 A | * | 9/1966 | Lamoureaux | 220/90 |
| 3,395,828 A | * | 8/1968 | Schnabel | 220/90 |
| 3,428,213 A | * | 2/1969 | Stephens | 220/90 |
| 3,610,461 A | * | 10/1971 | Allyn | 220/54 |
| 4,266,686 A | * | 5/1981 | Carter | 220/90 |
| 4,890,807 A | * | 1/1990 | Desjardins | 248/146 |
| 4,927,046 A | * | 5/1990 | Armstrong | 220/90 |
| 5,033,704 A | * | 7/1991 | Kerr | 248/110 |
| 5,174,965 A | * | 12/1992 | Jones et al. | 422/102 |
| 5,178,354 A | * | 1/1993 | Engvall | 248/316.7 |
| 5,202,094 A | * | 4/1993 | Jones et al. | 422/102 |
| 5,244,113 A | * | 9/1993 | Stymiest | 220/710.5 |
| D353,669 S | | 12/1994 | Jones et al. | D24/122 |
| D357,066 S | | 4/1995 | Jones et al. | D24/122 |
| 5,422,076 A | * | 6/1995 | Jones | 422/102 |
| D368,135 S | | 3/1996 | Vasai | D24/122 |
| 5,558,840 A | * | 9/1996 | Jones et al. | 422/104 |
| 5,591,401 A | * | 1/1997 | Sayles | 422/58 |
| D379,655 S | | 6/1997 | Savignac | D24/122 |
| 5,738,242 A | * | 4/1998 | Paris | 220/735 |
| 5,743,425 A | * | 4/1998 | Ellis | 220/254 |
| 5,791,505 A | * | 8/1998 | Gilliland | 215/228 |
| 5,806,704 A | * | 9/1998 | Jamison | 220/212 |
| 5,829,342 A | * | 11/1998 | Lee | 99/348 |
| 5,913,450 A | * | 6/1999 | Runkel | 220/696 |
| 6,277,646 B1 | * | 8/2001 | Guirguis et al. | 436/165 |

* cited by examiner

Primary Examiner—Jill Warden
Assistant Examiner—Dwayne K Handy

(57) ABSTRACT

A specimen gathering device permitting a person to position the specimen gathering device without contact with the specimen. The device includes a container member having an overlying lid and detachable handle assembly diametrically overlying the lid and forming a lever for tightening and loosening the lid. Releasable gripping members on the container wall, handle and lid permit manual separation of the handle and lid and supporting the container remote from a person's hand by one end portion of the handle.

7 Claims, 2 Drawing Sheets

COMBINED SPECIMEN CUP, LID AND DETACHABLE HANDLE

CROSS REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

This invention relates to a specimen cup for body fluids, such as urine, having a detachable handle and a lid cooperating with the handle to hold the handle in place when not in use.

Physician offices, hospitals and private labs use specimen cups to obtain body fluids such as urine, sputum and stool samples from patients. The patients are usually expected to give biological samples in the privacy of the restroom at the medical facility. The patient must hold the specimen cup while the sample is obtained. The person holding the specimen cup will sometimes soil their hand when collecting the specimen. This is particularly a problem for pregnant or obese patients, children, the elderly and many disabled patients. Soiling of the hand is also a frequent problem when a collection from midstream urine must be obtained.

This invention overcomes this problem to a great extent by providing a detachable handle which holds the specimen cup in an extended position relative to the holdert's hand and provides a lid for tightly securing the specimen in the cup, particularly when the specimen is obtained at home and carried to the medical facility.

2. Description of the Prior Art

The most pertinent patents are believed to be U.S. Pat. No. Des. 353,669 issued Dec. 20, 1994 and U.S. Pat. No. Des. 357,066 issued Apr. 4, 1995; both issued to Jones, et al. for Combined Specimen Cup And Detachable Handle.

U.S. Pat. No. Des. 368,135 issued Mar. 19, 1996 to Vasai for Urine Sample Cup Holder and U.S. Pat. No. Des. 379,655 issued Jun. 3, 1997 to Savignac for Urinary Specimen Collector are believe are good examples of the further state of the crowded art each showing a handle extending laterally from its specimen cup.

BRIEF SUMMARY OF THE INVENTION

The specimen cup comprises an annular wall having a helical thread about its outer upper end periphery for threadedly receiving a lid and includes a flat bottom for holding the specimen within the wall forming the cup. Basically the lid portion comprises a flat top with a depending wall having a helical thread on its inner wall surface cooperating with the thread on the outer surface of the cup open end portion. The lid is further provided with an eccentric upstanding cylindrical prong and an eccentrically positioned lug adjacent the perimeter of the cup top and on a diametric line with respect to the upstanding lug. An elongated handle member having a length at least spanning the diameter of the lid when the handle is horizontally disposed thereon. The handle member is characterized by a flat top surface having a coextensive depending wall portion defining a downwardly open recess when the handle overlies the lid. An apertured boss within the handle recess intermediate its ends frictionally receives the upstanding prong when the handle is diametrically disposed across the lid. The one end of the handle having an aperture cooperatively receiving the upstanding lug thus forming a lever for threadedly tightening or loosening the lid on the specimen cup. The outer wall of the cup adjacent but downwardly spaced from the depending limit of the lid wall is provided with a laterally and upwardly inclined limb which cooperatively receives the aperture in the end of the handle in a fulcrum action on the limb in which the end surface of the handle adjacent the aperture flatly bears against the outer surface of the cup sidewall and permits the user to hold the end of the handle opposite the cup in an extended fashion, safely out of contact with a stream of urine or the like.

The principal object of this invention is to provide an improved specimen cup having a detachable handle which permits a person to gather a specimen without contact with the specimen. A further object being to provide a lid connected handle which forms a lever for tightening or loosening the lid on the specimen cup.

DETAILED DESCRIPTION OF THE INVENTION

Figure 2:
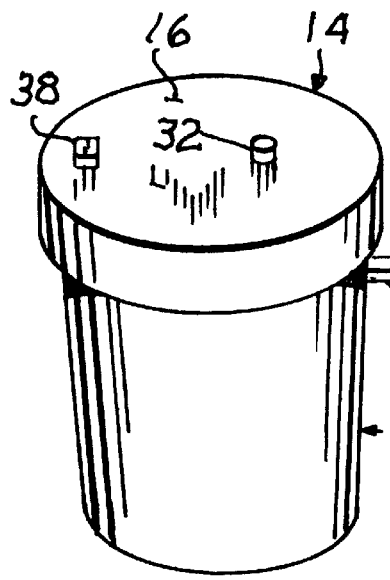
FIG. 2 is a similar perspective view of the cup and lid.

The reference numeral 10 indicates a specimen cup having an annular upstanding wall 12 forming an open top 14. The cup is provided with a removable lid 14 having a flat top surface 16 and a depending annular wall 18. The outer surface of the cup wall 12 adjacent its open end and the inward surface of the cup wall 18 are cooperatively provided with helical threads 20 for manually tightening or loosening the lid and sealing the open top of the container 10.

An elongated handle 22 normally diametrically overlies and projects beyond the perimeter of the lid 14. The handle 22 is channel-like in transverse section being provided with a coextensive top wall 23 having a coextensive depending wall forming parallel side walls 26 and defining a coextensive recess 28 within the walls 26. A centrally apertured upstanding boss 30, intermediate the length of the handle, is rigidly secured to the undersurface of the handle top wall 23 which cooperatively receives an upstanding cylindrical plug 32 eccentrically formed in upstanding relation on the lid top wall 16. The end portion of the handle top wall 23, opposite its top surface serrations 34, is provided with a rectangular aperture 36 which cooperatively loosely receives an upstanding rectangular lug 38 similarly eccentrically formed on the lid surface 16 and cooperatively enters the handle aperture 36 when the handle is diametrically disposed in the position of FIG. 1. The handle end wall 37 adjacent its aperture 36 is angularly beveled or inclined outwardly for the purposes presently explained. The purpose of the handle when joined with the lid plug 32 and lug 38 is to form a lever for manually rotating the lid 14 angularly in a thread tightening or loosening direction and closing the specimen cup 10.

Figure 1:
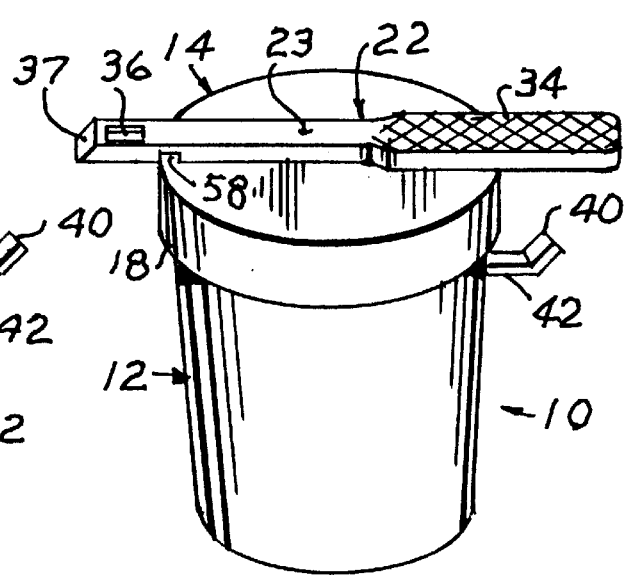
FIG. 1 is a perspective view of the specimen cup with the detachable handle horizontally secured on the upper surface of the specimen cup lid.
Figure 3:
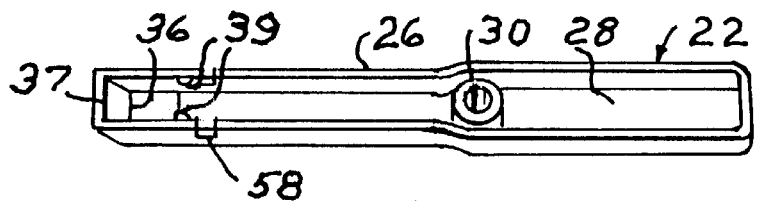
FIG. 3 is an inverted perspective view of the handle to a larger scale.
Figure 4:
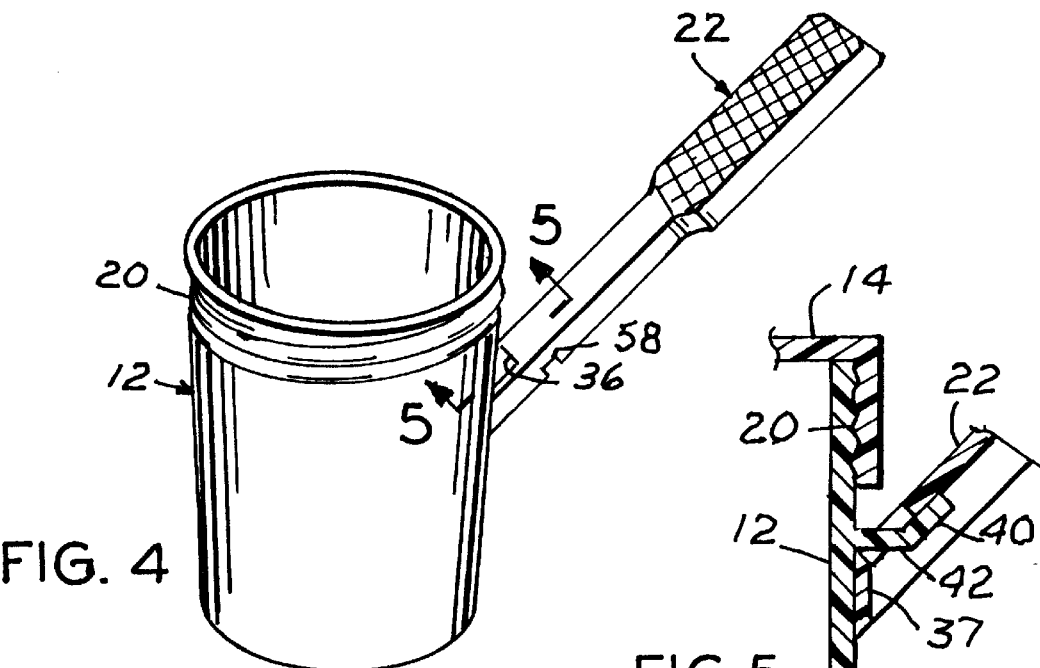
FIG. 4 is a perspective view similar to FIG. 1 illustrating the handle attached to the specimen cup.
Figure 5:
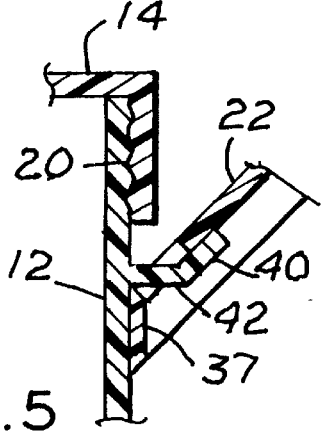
FIG. 5 is a fragmentary cross sectional view, to a further enlarged scale, taken substantially along the line of 5—5 of FIG. 4; and, FIG. 6 is a perspective view of an alternative embodiment illustrating the handle in stored position by dash lines.

The handle may be manually removed from the lid and when disposed in the position of FIG. 1 the aperture 36 cooperatively receives the upstanding angular end portion 40 on a handle horizontal limb 42 projecting outwardly from the specimen cup wall 12. As best illustrated by FIG. 4 the angular inclined end wall 37 of the handle is manually fulcrumed against the outer surface of the cup wall 12 by the inner surface of the handle wall 23 contacting the surface of the upwardly inclined portion 40 facing the cup wall 12 in a lifting and holding action of cup 10 by the handle 22 when the serrated end portion 34 of the handle is manually grasped, thus permitting the cup to be extended from the position of a holder's hand, not shown, when collecting a specimen. Additionally as best illustrated by FIG. 3, the handle wall 26 is provided with a pair of relatively small protrusions 39 disposed in opposed confronting relation on the inner surface adjacent the edge of the side wall 26 opposite the inner surface of the handle wall 23. The protrusions 39 are of selected configurations, such as substantially hemispherical, and permit the passage of opposing sides of the upwardly inclined end portion 40 in a snap action by outward flexing of the handle parallel sidewall portions.

Figure 6:
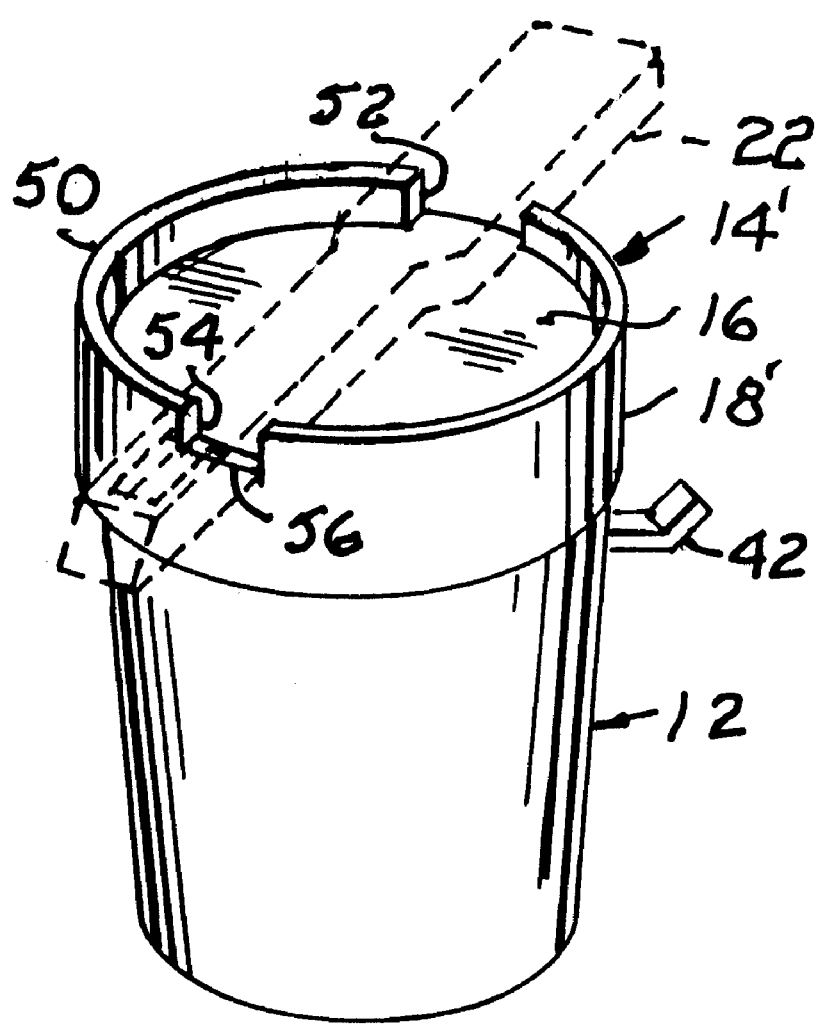

Referring now, more particularly to FIG. 6, an alternative embodiment of the lid is indicated by the numeral 14' in which the annular wall 18' of the lid is extended upwardly above the horizontal limit of the lid top surface 16 to form an annular upstanding rim 50 of selected height, slightly less than the vertical dimension of the handle side walls 26. The rim 50 is bisected to form diametrically opposite slots 52 and 54. The slot 52 projects upwardly from the horizontal surface of the lid 16 while the slot 54 terminates intermediate the distance between the upper limit of the rim 50 and the horizontal surface of the lid top 16 to form a ridge 56 which cooperatively nests opposing notches 58 formed in the handle sides 26 adjacent its end portion having the aperture 36. In this embodiment the handle 22 may similarly be used to loosen or tighten the lid 14'.

Obviously the invention is susceptible to changes or alterations without defeating its practicability. Therefore, I do not wish to be confined to the preferred embodiment(s) shown in the drawing(s) and described herein.

I claim:

1. A specimen cup comprising;

container means for receiving and retaining a specimen, the container means having an annular wall defining a specimen retaining cavity and having an open upper end communicating with the specimen receiving cavity, said container wall having an outer surface and having a laterally projecting horizontal limb terminating in an angularly upward projecting end portion adjacent the upper open end portion of said container wall;

lid means for opening and closing the upper end of said specimen receiving cavity, the lid means comprising a planar top surface having a depending internally threaded annular wall for surrounding and cooperatively threadedly engaging the outer surface of the wall defining the specimen cavity;

elongated handle means for supporting and positioning the container means to receive specimen within the specimen receiving cavity, the handle means comprising a channel shaped member having a coextensive bight portion and parallel side walls integrally joined with first and second end walls, said first end wall having an outer surface angularly inclined outwardly, a lug secured to the lid top surface adjacent the perimeter of the lid top surface;

an upstanding plug eccentrically secured on the lid top surface diametrically opposite the lug; and, a centrally apertured boss secured to the handle intermediate its ends and between said parallel side walls for nesting said plug when the handle means is diametrically disposed on the lid top surface with the handle bight aperture surrounding the lug, whereby said handle means serves as a lever for manually tightening or loosening the lid on the container means, the handle bight portion having a through aperture adjacent the outwardly inclined end wall for receiving and nesting the upward projecting portion of said limb between the side walls of the handle and cooperatively disposing the outer surface of said handle first end wall in lifting contact with the outer surface of said container wall whereby, a person gripping the handle end portion opposite the bight aperture can readily position the container for receipt of the specimen without contact with the specimen.

2. A specimen cup comprising;

container means for receiving and retaining a specimen, the container means having an annular wall defining a specimen retaining cavity and having an open upper end communicating with the specimen receiving cavity, said container wall having an outer surface and having a lateral limb terminating in an angularly upward projecting end portion adjacent the upper open end of said container wall; and, elongated detachable handle means for supporting and positioning the container means to receive specimen within the specimen receiving cavity, the handle means comprising a channel shaped member having a coextensive bight portion and parallel side walls integrally joined with first and second end walls, said first end wall having an outer surface angularly inclined outwardly, the handle bight portion having a through aperture adjacent the outwardly inclined end wall for receiving and nesting the upward projecting portion of said limb between the side walls of the handle and cooperatively disposing the outer surface of said handle first end wall in lifting contact with the outer surface of said container wall so that a person gripping the handle end portion opposite the bight aperture can readily position the container for receipt of the specimen without contact with the specimen.

3. The specimen cup according to claim 2 and further including:

lid means for opening and closing the upper end of said specimen receiving cavity, the lid means comprising a planar top surface and a depending annular wall surrounding and cooperatively threadedly engaging the outer surface of the wall defining the specimen cavity.

4. The specimen cup according to claim 1 and further including:

confronting protrusions disposed on the inner surface of said handle side walls adjacent the side wall surface opposite the bight portion and in the path of movement of said angular upwardly inclined portion toward and away from the handle bight portion.

5. The specimen cup according to claim 2 and further including:

confronting protrusions disposed on the inner surface of said handle side walls adjacent the side wall surface opposite the bight portion and in the path of movement of said angular upwardly inclined portion toward and away from the handle bight portion.

6. The specimen cup according to claim 1 and further including:

an annular rim projecting above said lid top surface a distance not greater than the vertical dimesion of said handle side walls, said rim having diametrically opposite upwardly open slots cooperatively receiving said handle when disposed therein.

7. The specimen cup according to claim 6 in which said handle side walls are provided with downwardly open notches, adjacent the end portion having the aperture, respectively nesting underlying portions of the rim forming one of the slots.

* * * * *